US00PP19058P2

(12) United States Plant Patent
Utecht

(10) Patent No.: US PP19,058 P2
(45) Date of Patent: Jul. 29, 2008

(54) *PELARGONIUM* PLANT NAMED 'FISTANSAL'

(50) Latin Name: *Pelargonium×hortorum*
Varietal Denomination: Fistansal

(76) Inventor: Angelika Utecht, Hinterer Rebstock 38, Montabaur (DE), 56410

( * ) Notice: Subject to any disclaimer, the term of this patent is extended or adjusted under 35 U.S.C. 154(b) by 0 days.

(21) Appl. No.: 11/803,251

(22) Filed: May 14, 2007

(51) Int. Cl.
*A01H 5/00* (2006.01)

(52) U.S. Cl. ..... Plt./327
(58) Field of Classification Search ..... Plt./327
See application file for complete search history.

*Primary Examiner*—Kent L. Bell
*Assistant Examiner*—S. B. McCormick-Ewoldt
(74) *Attorney, Agent, or Firm*—Jondle & Associates, P.C.

(57) ABSTRACT

A new cultivar of *Pelargonium* particularly characterized by bi-colored, salmon-pink and nearly white, semi-double flowers, medium-sized inflorescences on reddish peduncles, dark-green, relatively small leaves with medium zonation, a moderately vigorous growth habit and a medium to tall, rounded and moderately tight plant habit and an early to mid-season and floriferous flowering response, is disclosed.

1 Drawing Sheet

Genus and species: *Pelargonium×hortorum.*
Variety denomination: 'Fistansal'.

BACKGROUND OF THE NEW PLANT

The present invention comprises a new and distinct cultivar of *Pelargonium,* botanically known as *Pelargonium× hortorum,* and hereinafter referred to by the cultivar name 'Fistansal'. The new cultivar is a product of a planned breeding program which had the objective of creating new varieties having pink flowers, good flower color stability, medium-green foliage and vigorous growth. 'Fistansal' was discovered as a seedling resulting from a cross between the proprietary female parent 'K93-401-15' (unpatented), a *pelargonium* having light-salmon, semi-double flowers and the proprietary male parent 'K93-484-4' (unpatented), a *pelargonium* having single-type, light-salmon flowers. A single plant selection was chosen for further evaluation and for asexual propagation in 2003.

The new cultivar was created in 2002 in Hillscheid, Germany and has been asexually reproduced repeatedly by vegetative cuttings in Galdar, Gran Canaria, Spain, and Hillscheid, Germany over a 3- to 4-year period. 'Fistansal' has not been observed under all possible environmental conditions, thus the phenotype may vary significantly with variations in the environment such as temperature, light intensity, and day length. 'Fistansal' has been found to retain its distinctive characteristics through successive asexual propagations.

Plant Breeder's Rights for this cultivar were applied for in Germany on Apr. 25, 2006 and in Canada on Apr. 26, 2006.

SUMMARY OF THE INVENTION

The following are the most outstanding and distinguishing characteristics of this new cultivar when grown under normal horticultural practices in Hillscheid, Germany.

1. Bi-colored, salmon-pink and nearly white, semi-double flowers;
2. Medium-sized inflorescences on reddish peduncles;

3. Dark-green and relatively small leaves with medium zonation;
4. A moderately vigorous growth habit and a medium to tall plant habit;
5. A rounded and moderately tight plant habit; and
6. An early to mid-season and floriferous flowering response.

DESCRIPTION OF THE PHOTOGRAPH

This new *pelargonium* plant is illustrated by the accompanying photograph which shows blooms, buds, and foliage of the plant; the colors shown are as true as can be reasonably obtained by conventional photographic procedures. The photograph is of an un-pinched plant about 14-weeks-old and grown from rooted cuttings in a 14-cm pot under greenhouse conditions which approximate those generally used in commercial practice.

DESCRIPTION OF THE NEW CULTIVAR

The following detailed descriptions set forth the distinctive characteristics of 'Fistansal'. The data which define these characteristics were collected from asexual reproductions carried out in Hillscheid, Germany. The plant history was taken on 10-week-old, un-pinched plants in 12-cm pots in a greenhouse in mid-May 2006. The color readings were determined under natural light in mid-May from flowers grown in a greenhouse. Color references are to the R.H.S. Colour Chart of The Royal Horticultural Society of London (R.H.S.) (2001).

DETAILED BOTANICAL DESCRIPTION

Classification:
*Botanical.*—*Pelargonium×hortorum.*
*Common name.*—Zonal geranium.
Parentage:
*Female parent.*—'K93-401-15' a proprietary (unpatented) *pelargonium* having light-salmon, semi-double flowers.

*Male parent.*—'K93-484-4' a proprietary (unpatented) *pelargonium* having light-salmon, single-type flowers.

Plant:

*Form.*—Shrub, self-branching, rounded shape.

*Branching habit.*—5.2 branches per plant.

*Height.*—11.1 cm for a 10-week-old plant (measured from base of stem to the tips of the branches, excluding the inflorescences).

*Width.*—21.9 cm for a 10-week old plant.

*Time to produce a finished flowering plant.*—For the spring flowering response in Hillscheid, Germany in 2006, after 7 weeks from the planting of rooted cuttings, 50% of plants were flowering with at least one open flower.

*Outdoor plant performance.*—Plants continuously flower; a flower count in mid-September of 2006 in Hillscheid, Germany indicated about 15-20 inflorescences per plant.

Leaves:

*Arrangement.*—Alternate; opposite at flowering stems.

*Color, immature leaf.*—Upper surface: RHS 137A. Lower surface: RHS 138A.

*Color, mature leaf.*—General: Dark-green. Upper surface: RHS 137A. Lower surface: RHS 138A.

*Length.*—4.5 cm to 5.0 cm.

*Width.*—7.5 cm.

*Zonation color.*—RHS 200A (dark brown) with medium distinctness.

*Zonation diameter.*—Inner diameter of the ring is 3.5 cm and the band or belt of zonation is about 1.0 cm wide.

*Shape.*—Round to kidney-shaped with nearly no lobes and the gap between lowest lobes is mostly closed or even slightly overlapping.

*Apex.*—Rounded.

*Base.*—Cordate.

*Margin.*—Bi-crenate and slightly wavy.

*Texture.*—Upper surface is dull and velvety.

Petioles:

*Length.*—4.0 cm to 6.0 cm.

*Diameter.*—0.2 cm to 0.3 cm.

*Color.*—RHS 144B (light-green).

*Texture.*—Covered with fine pubescence.

Stems:

*Length.*—5.0 cm to 9.0 cm.

*Stem diameter.*—0.5 cm to 0.7 cm.

*Internode length.*—1.0 cm to 1.5 cm.

*Stem diameter.*—0.6 cm to 0.7 cm at middle portion.

*Color.*—Mainly RHS 143B (green) and partly infused with RHS 179B (reddish) anthocyanin.

*Texture.*—Appear smooth, yet covered with very short pubescence.

Flower buds (just before petals unfold):

*Length.*—1.8 cm.

*Width.*—1.0 cm to 1.2 cm.

*Shape.*—Elliptical.

*Color of sepals.*—RHS 143A to RHS 143B (light-green).

*Color of petals.*—RHS 49C (pale pink).

Inflorescence:

*Type.*—An umbel composed of about 40 to 60 flowers and buds.

*Umbel diameter.*—9.7 cm.

*Umbel depth (height).*—4.5 cm to 5.0 cm.

*Umbel shape.*—Nearly semi-spherical.

*Lastingness of the umbel on the plant.*—About 16 to 18 days.

*Peduncle.*—Length: 13.7 cm. Diameter: 0.4 cm to 0.6 cm. Texture: Pubescent with dense, short glandular hair. Color: Mainly RHS 166A (brownish).

*Pedicel.*—Length: 2.5 cm. Diameter: 0.15 cm. Texture: Pubescent with very short glandular hair. Color: RHS 144A and RHS 138A at the base; the upper portion is infused with RHS 178A anthocyanin.

Corolla:

*Diameter.*—4.7 cm.

*Depth.*—1.3 cm to 1.7 cm.

*Form.*—Semi-double.

*Shape.*—Irregular cup-shape.

*Color (overall).*—In general, salmon-pink with lighter nearly white margin.

*Number of petals.*—7 to 10.

*Petaloids.*—Number: 0 to 2. Shape: Variable; shorter and narrower than the petals and often folded or twisted. Color: RHS 50C or RHS 49A.

*Lastingness of individual flowers on the plant.*—6 to 8 days at 18° C.

*Fragrance.*—Absent.

Petals:

*Upper petals.*—Length: 2.5 cm. Width: 1.7 cm to 1.9 cm. Color: Upper surface: RHS 50D or RHS 49D to nearly white at the margin. Basal part: RHS 41C to RHS 41D. Lower surface: RHS 49A to RHS 56D. Markings: Very weak RHS 54A (pink) stripes.

*Lower petals.*—Length: 2.1 cm to 2.3 cm. Width: 1.8 cm to 1.9 cm. Color: Upper surface: RHS 50D or 49D to nearly white at the margin. Basal part: RHS 43C to RHS 43D. Lower surface: From RHS 49A to RHS 56D, somewhat variable. Markings: Absent.

*Shape.*—Obovate.

*Apex.*—Rounded but occasionally retuse.

*Base.*—Broadly acute.

*Margin.*—Entire.

*Texture.*—Smooth and slightly glossy.

Sepals:

*Number.*—5.

*Length.*—1.0 cm to 1.1 cm.

*Width.*—0.4 cm for the largest, upper sepal and 0.2 cm to 0.3 cm for the other sepals.

*Shape.*—Lanceolate.

*Apex.*—Acute.

*Base.*—Fused.

*Margin.*—Entire.

*Texture.*—Short pubescence.

*Color.*—Upper (outer) surface: RHS 143A (green) and the base is RHS 179A (red-purple). Lower (inner) surface: RHS 143B.

Reproductive organs:

*Androecium.*—Number of anthers: Most often 5. Filament color: Mainly RHS 155D (white) to RHS 43D at the tip. Filament length: 0.7 cm. Pollen color: RHS 28A (orange). Pollen amount: Moderate (typical).

*Gynoecium.*—Pistil number: 1. Pistil length: 0.8 cm to 0.9 cm. Stigma color: RHS 43C. Stigma shape: 5 to 6 lobed. Style color: RHS 43C. Style length: 0.6 to 0.7 cm. Style shape: Filiform (filament-like) with the lobes of the stigma at right angles.

Fruit/seed set: No seed set observed.

Disease and insect resistance: No special observations made; average susceptibility or tolerance (not resistant to diseases and pests common to the species).

COMPARISON WITH PARENTAL AND COMMERCIAL CULTIVARS

'Fistansal' differs from the female parent 'K93-401-15' (unpatented) in that 'Fistansal' has a stronger zonation on the leaves, develops more branches and has a more evenly rounded plant habit than 'K93-401-15'.

'Fistansal' differs from the male (pollen) parent 'K93-484-4' (unpatented) in that 'Fistansal' has semi-double flowers (more than 5 petals), while 'K93-484-4' has single-type flowers (only 5 petals). Additionally, 'Fistansal' grows more vigorously and develops more umbels (inflorescences) than 'K93-484-4'.

'Fistansal' differs from the commercial variety 'Fisrolisa' (U.S. Plant Pat. No. 13,193) in that 'Fistansal' has narrower petals and smaller inflorescences than 'Fisrolisa'. Additionally, 'Fistansal' has dark-green leaves, while 'Fisrolisa' has medium-green leaves.

'Fistansal' differs from the commercial comparison variety 'Fisvita' (U.S. Plant Pat. No. 15,011) in that 'Fistansal' has dark-green foliage, while 'Fisvita' has medium-green foliage. Additionally, 'Fistansal' has a slightly deeper salmon flower color (in the middle part of the flower) than 'Fisvita'.

I claim:

1. A new and distinct cultivar of *Pelargonium* plant as shown and described herein.

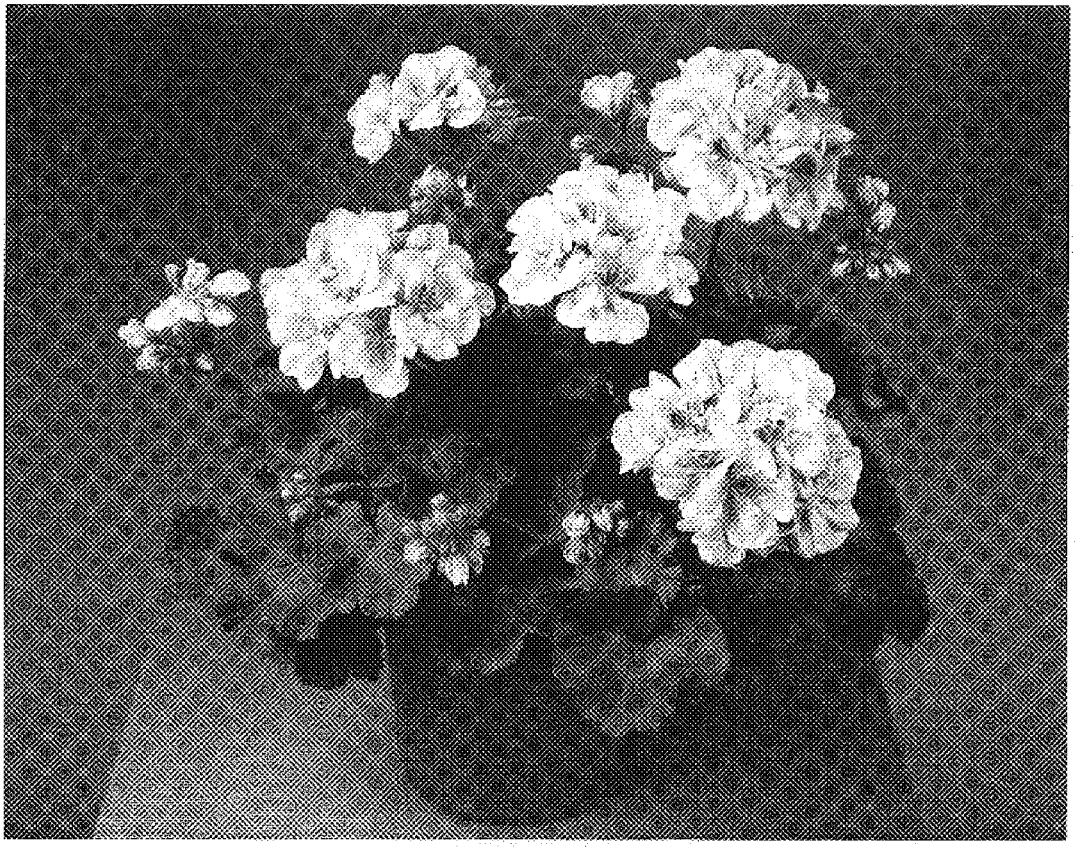

* * * * *